Patent Number: 4,567,184
… Date of Patent: Jan. 28, 1986

[54] CERTAIN ARYL OR HETERO-ARYL DERIVATIVES OF 1-HYDROXY-PENTANE OR 1-HYDROXY-HEXANE WHICH ARE USEFUL FOR TREATING INFLAMMATION AND ALLERGIES

[75] Inventors: John H. Musser, Malvern, Pa.; Utpal R. Chakraborty, Orangeburg, N.Y.

[73] Assignee: USV Pharmaceutical Corporation, Tuckahoe, N.Y.

[21] Appl. No.: 530,811

[22] Filed: Sep. 9, 1983

Related U.S. Application Data

[63] Continuation-in-part of Ser. No. 445,876, Dec. 1, 1982.

[51] Int. Cl.$^4$ .................. C07D 213/30; C07D 215/14; A61K 31/44; A61K 31/47
[52] U.S. Cl. .................... 514/277; 514/307; 514/311; 514/350; 514/356; 514/544; 514/568; 514/721; 546/149; 546/152; 546/322; 546/326; 546/344; 560/64; 562/465; 568/633; 568/644; 568/645
[58] Field of Search ............... 546/339, 344, 149, 152, 546/322, 326; 562/465; 560/64; 568/644, 645, 633; 514/544, 568, 307, 311, 356, 350, 277, 721

[56] References Cited

U.S. PATENT DOCUMENTS 4,200,763  4/1980  Dai ........................................ 560/109
4,202,833  5/1980  Dai ........................................ 260/463

FOREIGN PATENT DOCUMENTS 124777  9/1980  Japan ................................... 549/349

Primary Examiner—Alan L. Rotman
Attorney, Agent, or Firm—Scully, Scott, Murphy & Presser

[57] ABSTRACT

Compounds of the structure

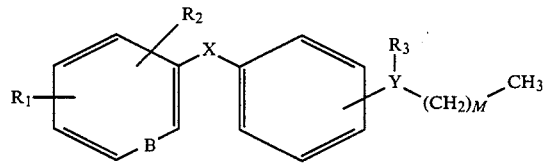

and pharmaceutically acceptable salts thereof, wherein $R_1$ and $R_2$ are independently hydrogen, alkyl, carboxy, alkylcarboxy, arylcarboxy, alkyl carbalkoxy, alkanoyl, formyl, nitrile, amino, amino alkyl, alkylamine, carboxamide, halo, trihalomethyl, hydroxy, alkoxy, aryloxy, nitro, sulfonyl, sulfonamide, thio, alkylthio, or $R_1$ and $R_2$ can be taken together to form a phenyl ring;
B is C or N, in which N can be in any position of the ring;
X is O, S, $NR_4$, $CH_2Z$, CH=N, CH=CH, C≡C, $CH_2ZCH_2$, C=O, C=CR or WC=O;
Y is $CHCH_2$, C=CH, C—$CH_2$, $CHCHR_5$, $CHC(R_5)_2$ or $CC(R_5)_2$;
$R_3$ is O, OH, $OR_4$, SH, $SR_4$, NH, $HNR_4$ or $N(R_4)_2$; and
M is an integer from 0 to 10; wherein Z is O, S or $NR_4$; $R_4$ is H, alkyl or aryl;
W is O, S or $NR_4$; and $R_5$ is H, alkyl or fluoro have antiinflammatory and antiallergic activities.

16 Claims, No Drawings

CERTAIN ARYL OR HETERO-ARYL DERIVATIVES OF 1-HYDROXY-PENTANE OR 1-HYDROXY-HEXANE WHICH ARE USEFUL FOR TREATING INFLAMMATION AND ALLERGIES

This application is a continuation-in-part of application Ser. No.: 445,876, filed Dec. 1, 1982.

DESCRIPTION OF THE INVENTION

This invention relates to new chemical compounds possessing valuable pharmaceutical activity. More particularly the invention relates to novel lipoxygenase inhibitor compounds possessing antiinflammatory and antiallergic activities and having the following formula:

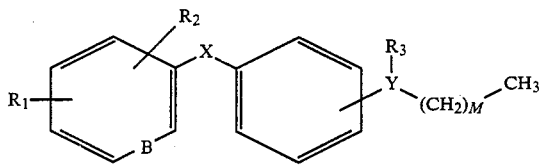

and pharmaceutically acceptable salts thereof, wherein
$R_1$ and $R_2$ are independently hydrogen, alkyl, carboxy, alkylcarboxy, arylcarboxy, alkyl carbalkoxy, alkanoyl, formyl, nitrile, amino, amino alkyl, alkylamine, carboxamide, halo, trihalomethyl, hydroxy, alkoxy, aryloxy, nitro, sulfonyl, sulfonamide, thio, alkylthio, or $R_1$ and $R_2$ can be taken together to form a phenyl ring;

B is C or N, in which N can be in any position of the ring;

X is O, S, $NR_4$, $CH_2Z$, $CH=N$, $CH=CH$, $C\equiv C$, $CH_2ZCH_2$, $C=O$, $C=CH$ or $WC=O$;

Y is $CHCH_2$, $C=CH$, $C-CH_2$, $CHCHR_5$, $CHC(R_5)_2$ or $CC(R_5)_2$;

$R_3$ is O, OH, $OR_4$, SH, $SR_4$, NH, $HNR_4$ or $N(R_4)_2$; and

M is an integer from 0 to 10;
wherein Z is O, S or $NR_4$; $R_4$ is H, alkyl, or aryl;
W is O, S or $NR_4$; and $R_5$ is H, alkyl or fluoro.

The alkyl groups in alkylcarboxy, carboxyalkyl, alkyl carboxyalkyl, alkylamine, amino alkyl, alkoxy, carbalkoxy, alkyl carbalkoxy, alkanoyl, alkylthio and in $NR_4$ and $CR_5$ contain from 1 to 6 carbon atoms and have either the straight or branched structure. Such groups include methyl, ethyl, propyl, isopropyl, butyl, isobutyl, amyl, isoamyl, hexyl, vinyl, allyl, propenyl, ethynyl, and the like.

The halo groups in halo and trihalomethyl contain F, Cl, Br or I.

The aryl groups in aryl, arylcarboxy and aryloxy are phenyl or naphthyl.

The preferred compounds are those in which: $R_1$ and $R_2$ are independently alkylcarboxy or $R_1$ and $R_2$ form an aromatic ring; the alkyl group in alkylcarboxy is methyl; B is C or N; X is $CH_2Z$; Z is O; Y is $CHCH_2$; $R_3$ is OH or $HNR_4$ and M is an integer from 2 to 3 inclusive.

The new compounds of the present invention can be prepared by art-recognized procedures from known starting materials and intermediates. A schematic representation of the synthesis is as follows:

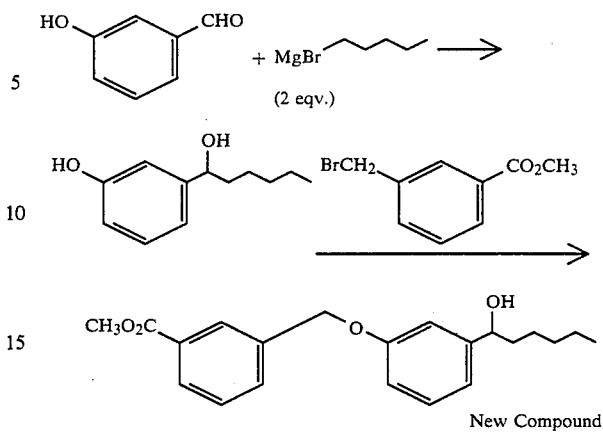

New Compound

The invention will be more fully illustrated in the examples that follow. These examples are given by way of illustration and are not to be considered as limiting.

EXAMPLE 1A

Methyl-2-bromomethylbenzoate

A water jacketted, immersion photolysis vessel equipped with a $N_2$ inlet, dropping funnel and a reflux condenser was charged with 1 L of carbon tetrachloride and 127 g. (0.847 mol) of 2-methyl toluate (Pfaltz and Bauer M29200). A solution of 400 ml carbon tetrachloride and 43.5 ml (0.849 mol) of bromine was added to the dropping funnel. After the solution had been heated to reflux the bromine solution was slowly added while the solution was irradiated with a 600 watt incandescent lamp. After the addition of the bromine solution was complete, the lamp was turned off and the solution cooled. The carbon tetrachloride was removed under reduced pressure. The resultant oil was crystallized from 250 ml of a (1:1) solution of diethyl ether and hexane. The solid was collected and washed with hexane to yield 119 g. (61%) of product.

In like manner, as above, using appropriate starting materials, the following compounds were prepared:
Methyl-3-bromomethylbenzoate;
Methyl-4-bromomethylbenzoate; and
Methyl-3-bromomethylphenylacetate.

EXAMPLE 1B

1-(3-Hydroxyphenyl)-1-pentanol

A dried 1 L 3-neck flask equipped with a $N_2$ inlet, reflux condenser, mechanical stirrer and a 500 ml dropping funnel was charged with 24.3 g (1.0 mol) of magnesium and 50 ml of anhydrous ether. To this was added 15 g. (0.11 mol) of 1-bromobutane (Aldrich 23,988-7) and one crystal of iodine. The dropping funnel was charged with 122 g. (0.89 mol) of 1-bromobutane and 100 ml of anhydrous ether. After the contents of the reaction flask began to reflux, the flask was cooled with a water/ice bath and the 1-bromobutane solution was added at such a rate as to maintain a gentle reflux. After the addition was complete the reaction mixture was refluxed for one-half hour, then cooled to 0° C. in an ice/water bath. The dropping funnel was then charged with 38.0 g (0.311 mol) of 3-hydroxybenzaldehyde (Aldrich H 1,980-8) and 250 ml of anhydrous ether. This slurry was added over a 1 hour period. After the addition the reaction mixture was allowed to warm up to room temperature and was stirred overnight. The reaction mixture was neutralized with 900 ml of 5% aqueous HCl. The reaction mixture was extracted with 2×500 ml of ethyl acetate, the organic extracts combined, washed with 1 L of water, dried over anhydrous sodium sulfate and concentrated under reduced pressure. The crude product was recrystallized from ethyl acetate to yield 44.0 g. (79%) of 1-(3-hydroxyphenyl)-1-pentanol, m.p. 120°–122° C.

In like manner as above, using appropriate starting materials and reagents, the following compounds were prepared:

1-(3-Hydroxyphenyl)-1-hexanol;
1-(2-Hydroxyphenyl)-1-hexanol;
2-(3-Hydroxyphenyl)-2-heptene;
1-(4-Hydroxyphenyl)-1-hexene;
Phenyl-3-[1-(hydroxy)hexyl]benzyl ether; and
1-(3-Phenoxyphenyl)-1-hexanol.

EXAMPLE 1C

Methyl-2-[[3-(1-hydroxypentyl)phenoxy]methyl]benzoate

To a 1 L 3-neck round bottom flask was added 45.2 g. (0.197 mol) of methyl O-bromomethylbenzoate, 35.5 g (0.197 mol) of 1-(3-hydroxyphenyl)-1-pentanol, 3.0 g (0.020 mol) of sodium iodide, 64.3 g. (0.198 mol) of cesium carbonate and 500 ml of acetone. This slurry was refluxed for 3½ days. At which time the reaction mixture was cooled, solid removed by suction filtration and the solvent removed under reduced pressure. The resulting oil was partitioned between 10% aqueous HCl and ethyl acetate. The organic extract was washed with 200 ml of water, dried over anhydrous sodium sulfate and concentrated to yield 65.2 g of oil. A silica gel chromatography using hexane/chloroform (1:2) as eluent afforded 54.7 g. (85%) of product as an oil.

In like manner as above, using appropriate starting materials and reagents, the following compounds were prepared:

Methyl-3-[[3-(1-hydroxyhexyl)phenoxy]methyl]benzoate;
Methyl-2-[[3-(1-hydroxyhexyl)phenoxy]methyl]benzoate;
Methyl-4-[[3-(1-hydroxyhexyl)phenoxy]methyl]benzoate;
Methyl-3-[[2-(1-hydroxyhexyl)phenoxy]methyl]benzoate;
Methyl-3-[[3-(1-hydroxyhexyl)phenoxy]methyl]phenylacetate;
3-[[3-(1-Hydroxyhexyl)phenoxy]methyl]benzonitrile;
Methyl-2-[4-[[3-1-hydroxyhexyl)phenoxy]methyl]-phenoxy]acetate;
Benzyl-3-[1-(hydroxy)hexyl]phenyl ether;
Methyl-3-[[3-1-methyl-1-hexenyl)phenoxy]methyl benzoate;
Methyl-3-[[4-(1-hexenyl)phenoxy]methyl benzoate;
6-[[3-(1-Hydroxyhexyl)phenoxy]methyl]picolinyl nitrile;
Phenyl-3-cyanobenzyl ether;
3-(1-Hydroxyhexyl)phenyl-3-trifluoromethylbenzyl ether;
2-(3-(1-Hydroxyhexyl)phenoxy methyl naphthalene;
2-(3-(1-Methyl-1-hexenyl)phenoxy)methyl quinoline hydrochloride.

EXAMPLE 2

2-[[3-(1-Hydroxyhexyl)phenoxy]methyl]benzoic acid

A solution of methyl-2-[[3-(1-hydroxyhexyl)phenoxy]methyl]benzoate (1.0 g.) in 50 ml of methanol was treated with 1N aqueous sodium hydroxide. The reaction was stirred for 1 hour at room temperature. The mixture was washed with ethyl ether, acidified with 5% aqueous hydrochloric acid and extracted with chloroform. The chloroform extract was dried (MgSO$_4$) and concentrated to a solid (0.7 g., 73% yield), m.p. 76°–80° C.

In like manner as above, using appropriate starting materials, the following compounds were prepared:

3-[[3-1-Hydroxyhexyl)phenoxy]methyl]benzoic acid;
2-[[3-1-Hydroxyhexyl)phenoxy]methyl]benzoic acid, m.p. 115°–115.5° C.;
4-[[3-(1-Hydroxyhexyl)phenoxy]methyl]benzoic acid, m.p. 105°–6° C.;
3-[[3-(1-Hydroxyhexyl)phenoxy]methyl]phenyl acetic acid; and
6-[[3-(1-Hydroxyhexyl)phenoxy]methyl]picolinic acid, m.p. 111°–113° C.

EXAMPLE 3

Methyl-3-[[3-(1-acetoxyhexyl)phenoxy]methylbenzoate

To a solution of methyl-3-[[3-(1-hydroxyhexyl)phenoxy]methyl]benzoate (1.7 g.) in pyridine at 0° C. was added acetic anhydride (2.7 ml). The reaction was stirred for four days at room temperature. The solvent was removed in vacuo and the remaining oil was purified by HPLC on silica gel using a hexanes/ethyl acetate in 9:1 ratio as an eluent (1.1 g., 57% yield).

EXAMPLE 4

Methyl-3-[[3-(1-methoxyhexyl)phenoxy]methyl]benzoate

To a suspension of sodium hydride (0.5 g.) in ethyl ether at 0° C. was added methyl-3-[[3-(1-hydroxyhexyl)phenoxy]methyl]benzoate (1.7 g.) in ether. The mixture was allowed to warm to room temperature. Methyl iodide (0.6 ml) was added and the reaction was stirred at room temperature for three days. The reaction was quenched with saturated aqueous ammonium chloride. The mixture was extracted with ethyl ether. The organic extract was washed with water, dried (MgSO$_4$) and concentrated to an oil. The oil was purified by HPLC on silica gel using a 1:9 ratio of ethyl acetate/hexanes as an eluent.

EXAMPLE 5

Methyl-3-[[3-[1-(tetrahydro-2H-pyran-2-yloxy)hexyl]-phenoxy]methyl]benzoate

To a solution of methyl-3-[[3-(1-hydroxyhexyl)phenoxy]methyl]benzoate (2.2 g), dihydropyran (2.3 ml) and ethyl ether was added a catalytic amount of para-toluene sulfonic acid. The reaction was stirred at room temperature for four days. The ethyl ether was removed in vacuo and the remaining oil was purified by HPLC on silica gel using 7:93 ratio of ethyl acetate/hexanes as an eluent (1.8 g., 67% yield).

In like manner as above, using appropriate starting materials, the following compound was made:

Methyl-2-[[3-[1-(tetrahydro-2H-pyran-2-yloxy)pentyl]-phenoxy]methyl]benzoate.

EXAMPLE 6

2-[3-(1-Hydroxypentyl)phenoxy]methyl]benzenemethanol

To a suspension of lithium aluminum hydride (1.0 g.) in ethyl ether (100 ml) at 0° C. was added dropwise a solution of methyl-4-[[3-(1-hydroxyhexyl)phenoxy]methyl]benzoate (3.2 g.) in ethyl ether (100 ml). The reaction was consecutively quenched with 1 ml of water, 1 ml of 15% sodium hydroxide and 3 ml of water. The mixture was filtered and the ethyl ether was removed in vacuo (1.9 g., 65% yield).

EXAMPLE 7

3-[[3-(1-Hydroxyhexyl)phenoxy]methyl]benzaldehyde

To a solution of 3-[[3-(1-hydroxyhexyl)phenoxy]methyl]benzonitrile (10.0 g.) in THF was added diisobutylaluminum hydride (15 g.) and the reaction was refluxed overnight. Methanol (10.2 ml) was slowly added followed by water (5.7 ml). The mixture was filtered and the filtrate was concentrated to an oil. The oil was dissolved in chloroform. The solution was washed with 5% aqueous hydrochloric acid (4 times), dried (MgSO$_4$) and concentrated to an oil (3.0 g., 30% yield).

In like manner as above, using appropriate starting materials, the following intermediate was prepared:
Phenyl-3-formylbenzyl ether.

EXAMPLE 8

3-[[3-(1-Hydroxyhexyl)phenoxy]methyl]benzyl amine hydrochloride

To a suspension of lithium aluminum hydride (1.0 g.) in ethyl ether, was added dropwise a solution of 3-[[3-(1-hydroxyhexyl)phenoxy]methyl]benzonitrile (3.0 g.) in ethyl ether. After stirring for 2 hours at room temperature the reaction was quenched consecutively with 1 ml H$_2$O, 1 ml 15% sodium hydroxide and 3 ml of water. The mixture was filtered. The remaining solution was treated with ethereal hydrochloric acid and a precipitate formed. The precipitate was filtered and dried, giving 2.2 g (63% yield) of solid, m.p. 90°-94° C.

EXAMPLE 9

3-[[3-(1-hydroxyhexyl)phenoxy]methyl]benzamide

A mixture of 3[[3-(1-hydroxyhexyl)phenoxy]methyl]benzonitrile (5.0 g.), 30% hydrogen peroxide (6.6 ml), ethanol (9 ml) and 6N sodium hydroxide (0.7 ml) was stirred at room temperature for one hour. The reaction was then heated to 50° C. for three hours. The solution was neutralized with 5% aqueous hydrochloric acid and extracted with chloroform. The organic extract was dried (MgSO$_4$) and concentrated to a solid. The solid was recrystallized from ethyl acetate giving 3.4 g (63%) yield of solid, m.p. 97°-98° C.

In like manner as above, using appropriate starting materials, the following compound was prepared:
3-[3-hexanoyl phenoxy]methyl benzamide.

EXAMPLE 10

Benzyl-3-(hexanoyl)phenyl ether

To a suspension of pyridinium chlorochromate (32.3 g) in methylene chloride (200 ml) was added a solution of benzyl-3-[1-hydroxyhexyl]phenyl ether (28.4 g.) in methylene chloride (25 ml). The reaction was stirred at room temperature for 1½ hours. The excess methylene chloride was decanted and residual black solid was triturated with ethyl ether (four times.) The combined organic extract was purified on flurosil using ethyl ether as an eluent (27.5 g., 98% yield).

In like manner as above, using appropriate starting materials and reagents, the following compound was prepared:
3-[3-Hexanoyl phenoxy]methyl benzonitrile.

EXAMPLE 11

2-[[3-(1-Hydroxyhexyl)phenoxy]methyl]pyridine hydrochloride

A suspension of 3.3 g of picolyl chloride hydrochloride (Aldrich 16,270-1), 1-(3-hydroxyphenyl)-1-hexanol (3.9 g.), cesium carbonate (16.3 g.), cesium iodide (trace) and acetone was refluxed for 40 hours. The reaction was filtered through a pad of celite and silica gel and the solvent removed in vacuo. The remaining oil was dissolved in ethyl ether, filtered through celite and silica gel and treated with ethereal hydrochloric acid. The resulting white precipitate was filtered, washed (ethyl ether) and dried giving 4.2 g (66% yield) of solid, m.p. 164°-165° C.

In like manner as above, using appropriate starting materials and reagents, the following compounds were prepared:
3-[[3-(1-Hydroxyhexyl)phenoxy]methyl]pyridine hydrochloride, m.p. 162°-163° C.;
2-[[3-(1-Hydroxyhexyl)phenoxy]methyl]quinoline hydrochloride, m.p. 90°-95° C.; and
4-[[3-(1-Hydroxyhexyl)phenoxy]methyl]pyridine hydrochloride, m.p. 160°-160.5° C.

EXAMPLE 12

Methyl-6-[[3-(1-hydroxyhexyl)phenoxy]methyl]picolinate

A solution of 6[[3-(1-hydroxyhexyl)phenoxy]methyl]picolinyl nitrile (1.1 g.), methanol (50 ml) and cesium carbonate was stirred at room temperature overnight. The reaction mixture was diluted with 0.1N hydrochloric acid. After stirring for three hours, the methanol was removed in vacuo and the remaining suspension was extracted with chloroform. The organic extract was dried (MgSO$_4$) and concentrated to an oil (7.6 g., 94% yield).

EXAMPLE 13

Benzyl-3-[1-(N-methylamino)hexyl]phenyl ether

A solution of benzyl-3-(hexanoyl)phenyl ether (2.8 g.), 40% aqueous methylamine (1.5 ml) and methanol adjusted to pH 6 with 5% aqueous hydrochloric acid is treated with a methanolic solution of sodium cyanoborohydride. The reaction is stirred overnight. The methanol is removed in vacuo and the remaining mixture is extracted with methylene chloride. The organic extract is dried (MgSO$_4$) and concentrated to an oil.

In like manner as above, using appropriate starting materials, the following compounds can be prepared:
3-Chlorobenzyl-3-[1-(n-butylamino)hexyl]phenyl ether; and
2-Trifluoromethyl-3-[1-(N,N-dimethylamino)hexyl]phenyl ether.

EXAMPLE 14

Benzyl-3-[1-hydroxy-2,2-(dimethyl)hexyl]phenyl ether

To a solution of lithium amide (0.36 g.) and methyl iodide (3.02 g.) in THF (10 ml) at reflux is slowly added a solution of benzyl-3-(hexanoyl)phenyl ether (2.0 g) in THF (10 ml). The reaction is heated at reflux for two hours. The THF is removed in vacuo. The residue is dissolved in ethyl acetate, washed with water and brine; dried (MgSO$_4$) and concentrated to an oil. The oil is dissolved in ether and slowly added to a suspension of lithium aluminum hydride (0.1 g.) in ethyl ether. The reaction is then heated at reflux for two hours. The reaction is quenched by consecutive treatment with water (0.1 ml), 1N NaOH (0.3 ml), water (0.1 ml). The mixture is filtered and the ethyl ether is removed in vacuo giving the desired oil.

In like manner as above, using appropriate starting materials and reagents, the following compounds can be prepared:

2,4-Dibromobenzyl-3-[1-(hydroxy)2-(isobutyl)hexyl]phenyl ether; and

4-Fluorobenzyl-3-[1-(hydroxy)2-(diethyl)heptyl]phenyl ether; and Benzyl 3-(1-hydroxy-2-methyl hexyl)phenyl ether.

EXAMPLE 15

3-(1-Hydroxyhexyl)benzyl alcohol

To a solution of pentyl magnesium bromide (0.082 mol) in ethyl ether (100 ml) at 0° C. as prepared in Example 2 is added cadmium chloride (8.06 g) portionwise. The suspension is stirred overnight at room temperature. The solvent is distilled and toluene (300 ml) is added. The mixture is refluxed for one hour and cooled to room temperature. A solution of 3-carbomethoxybenzoyl chloride (48 g.) in toluene (50 ml) is slowly added. The reaction is refluxed for two hours. After cooling, 3% aqueous hydrochloric acid is added. The organic phase is separated and the aqueous phase is extracted with ethyl acetate. The combined extracts are dried (MgSO$_4$) and concentrated to an oil. The oil is dissolved in ethyl ether and slowly added to a suspension of lithium aluminum hydride (4.0 g.) in ethyl ether. The reaction is heated at reflux for two hours. The reaction was quenched by consecutive treatment with water (4 ml), 1N NaOH (12 ml) and water (4 ml). The mixture is filtered and the ethyl ether is removed in vacuo giving the desired oil.

EXAMPLE 16

Tolyl-3-(1-hydroxyhexyl)benzyl sulfonate

To a solution of 3-(1-hydroxyhexyl)benzyl alcohol (20.8 g.) in pyridine (50 ml) is added para-toluenesulfonyl chloride (20.1 g.). The reaction is stirred at room temperature for two days. Ice is added and the mixture is extracted with ethyl ether (twice). The organic extract is washed with 5% aqueous hydrochloric acid (four times), brine; dried (MgSO$_4$) and concentrated to an oil.

EXAMPLE 17

Methyl-3-[[3-(1-hydroxyhexyl)anilinyl]methyl]benzoate

A mixture of tolyl-3-(1-hydroxyhexyl)benzyl sulfonate (3.6 g.), methyl-3-aminobenzoate (1.5 g.) (Pfaltz and Bauer M10720), cesium carbonate (3.2 g.) and toluene (200 ml) is refluxed for two days. The reaction is filtered and concentrated to an oil. The oil is purified by HPLC on silica gel.

In like manner as above, using appropriate starting materials and reagents, the following compounds can be prepared:

Ethyl-2-[[3-(1-hydroxybutyl)anilinyl]methyl]benzoate;
Isopropyl-4-[[3-(1-hydroxybutyl)anilinyl]methyl]benzoate;
Methyl-3-[[2-(1-hydroxyhexyl)anilinyl]methyl]benzoate;
Phenyl-3-[1-(hydroxy)hexyl]benzyl thioether;
3-Methoxyphenyl-3-[1-(hydroxy)hexyl]benzyl thioether;
4-Nitrophenyl-3-[1-(hydroxy)hexyl]benzyl thioether; and
Methyl-2-[[3-(1-hydroxyhexyl)thiophenoxy]methyl]benzoate.

EXAMPLE 18

Methyl 3-[3-(1-hydroxyhexyl)phenyl)amino]carbonyl]benzoate

Dimethyl isophthalate (100 g) was mixed with potassium hydroxide (30 g) in methanol (700 ml) and water (500 ml), and refluxed for two hours. The reaction mixture was extracted thoroughly with ether to remove any unreacted diester present, and then the aqueous solution was acidified with cold, dilute HCl (6N). The white precipitate was filtered, dried and treated with ether-methanol. The insoluble diacid was filtered off, and the pure desired mono-ester was crystallized from the ether-methanol solution as a while solid (59 g).

A solution of methyl 3-carboxybenzoate (9 g), as prepared above, in methylene chloride (150 ml)-tetrahydrofuran (25 ml) solution was treated with oxalyl chloride (9.5 g), and dimethyl formamide (4 drops). The mixture was stirred at room temperature for one hour, and then all volatiles were removed by reduced pressure distillation. The acid-chloride of methyl 3-carboxybenzoate was obtained as a pale yellow liquid.

To a solution of the above acid chloride (9.9 g) in methylene chloride (75 ml) was added a mixture of triethylamine (6.3 g) and 3-aminobenzaldehyde diethylacetal (9.75 g); 3-aminobenzaldehyde diethylacetal was prepared by reducing (H$_2$, Pd-C, MeOH) 3-nitrobenzaldehyde diethyl acetal, which in turn was made by acetalization of 3-nitrobenzaldehyde with triethylorthoformate and p-toluenesulfonic acid in ethanol). The mixture of the acid chloride and the primary amine was stirred at room temperature overnight, and poured carefully into cold water. The organic layer was separated, dried over anhydrous magnesium sulfate, and then all solvent was removed. The residue was dissolved in tetrahydrofuran, and then dilute HCl solution (1N) was added till the mixture remained homogenous. This mixture was stirred at room temperature for one hour, and then most of the volatile solvent was removed. The aqueous solution was extracted with ethyl acetate, and the organic extract was washed with water, saturated sodium bicarbonate, and finally brine. All volatiles were removed, and the residual solid was crystallized from methanol-hexanes to give pure methyl 3-(3-formyl)phenylaminocarbonyl benzoate as a white solid.

The above aldehyde (1.5 g) was dissolved in dry tetrahydrofuran, and cooled in an ice bath. To this cold solution was added dropwise, a solution of pentylmagnesiumbromide (prepared from 1-bromopentane (1.9 g)

and magnesium turnings (0.31 g) in dry ether). The reaction mixture was stirred at 0° C. for two hours, and allowed to warm up to room temperature. The reaction mixture was carefully poured into cold water, and then extracted with ethyl acetate. The organic extract was washed with dilute HCl solution (0.1N), brine and then dried over anhydrous magnesium sulfate. All volatiles were removed to leave a viscous liquid (2 g) which quickly solidified on standing. This solid was crystallized from ethyl acetate-hexanes to give the pure desired material. In like manner, using appropriate starting materials and reagents, the following compound was prepared: 2-(3-(1-Hydroxyhexyl)phenylaminocarbonyl)benzoic acid, m.p. 114°–117° C.

EXAMPLE 19

Methyl 3-[3-[1-hydroxy-2,2-dimethylhexyl]phenoxy]methyl benzoate

A mixture of 3-(1-hydroxy-2,2-dimethylhexyl)phenol (0.7 g); prepared by the hydrogenolysis ($H_2$, 10% Pd-C, MeOH) of benzyl 3-(1-hydroxy-2,2-dimethylhexyl)phenyl ether made in Example 14), methyl 3-bromomethyl benzoate (0.72 g), potassium carbonate (0.45 g) and sodiuim iodide (0.05 g) in acetone (25 ml) was refluxed overnight. The reaction mixture was cooled, and poured into water. The aqueous solution was extracted with ethyl acetate. The organic extract was dried over magnesium sulfate, and then all volatiles were removed. The residual liquid (1.2 g) was purified by chromatography (silica gel; 18% ethyl acetate in hexanes) to isolate the desired ester as a clear, colorless liquid.

EXAMPLE 20

2-(3-Hexanoylphenoxy)methyl quinoline

A solution of 1-(3-hydroxyphenyl)-1-hexanol (3 g) (made in Example 1B) in methylene chloride (200 ml) was added to a well-stirred suspension of pyridinium chlorochromate (5.1 g) and sodium acetate (2.5 g) in methylene-chloride (150 ml). The mixture was stirred at room temperature for two hours. Ether (100 ml) was added, and the brown granular precipitate was removed by filtration. All volatiles were removed from the filtrate, and the residual liquid was purified by chromatography on silical gel using ether as eluent. The desired ketone, 3-hexanoylphenol, was isolated as a clear, colorless oil.

This ketone (1.2 g) was refluxed with 2-chloromethyl-quinoline hydrochloride (1.3 g), potassium carbonate (8.6 g), potassium iodide (0.05 g) and cesium carbonate (0.05 g) in acetone (300 ml) for 24 hours. The reaction mixture was filtered, and the filtrate was concentrated, dissolved in chloroform, and then washed with sodium hydroxide solution (5%), water and brine. After drying, all volatiles were removed. The residue was purified by chromatography on silica gel (25% ethyl acetate in hexanes). The pure desired product was isolated as a tan solid, m.p. 52°–55° C.

In like manner, using appropriate starting materials and reagents, the following compound was prepared: 2-(3-Hexanoylphenoxy)methyl naphthalene.

EXAMPLE 21

2-(3-Benzyloxyphenyl)-2-heptanol

To an ethereal solution of benzyl 3-hexanoylphenyl ether (3 g) made in Example 10 was added slowly an excess of methylmagnesium bromide, (2.5 g; 7.0 ml of a 3M solution in ether). The reaction mixture was stirred overnight. A saturated solution of ammonium chloride was added dropwise to the well-stirred reaction mixture until the solution became clear, and a gray-white solid coagulated to form a hard cake. The liquid was filtered, and the residue was washed with more ether. The ether layer was separated from the aqueous layer, washed with brine, and dried over magnesium sulfate. All volatiles were removed to give an oil, which was purified by chromatography on silica gel (6% ethyl acetate in hexanes) to get the desired tertiary alcohol as a clear, colorless liquid.

In like manner as above, using appropriate starting materials and reagents, the following compounds were prepared:
2-(3-Benzyloxyphenyl)-3,3-dimethyl-2-heptanol; and
2-(3-(2-(2-Hydroxyheptyl)phenoxy)methyl naphthalene.

EXAMPLE 22

2-(3-(3-(2-Hydroxy)heptyl)phenoxy)methyl quinoline hydrochloride

A mixture of 2-chloromethyl quinoline hydrochloride (3.1 g) and 2-(3-hydroxyphenyl)-2-heptanol(3 g; prepared from 3-hexanoylphenol (Example 20), and methyl magnesium bromide, in the same manner as described for 2-(3-benzyloxyphenyl)2-heptanol in Example 21) in acetone (300 ml) containing potassium carbonate (20 g) and potassium iodide (0.2 g) was refluxed overnight. The reaction mixture was cooled, and most of the volatiles were removed at the rotary evaporator. The residue was taken up in ethyl acetate, and was washed with sodium hydroxide solution (5%) and brine. The organic layer was dried over magnesium sulfate and all solvent was removed to leave the crude product (weighing about 6 g). This was purified by chromatography (silica gel; 20% ethyl acetate in hexanes). The free base, isolated as an oil, was dissolved in dry ether, and treated with hydrogen chloride gas to give the pure desired salt as a white solid, m.p. 125° C. (dec.).

In like manner as described above, using appropriate starting materials and reagents, the following compound was prepared:
2-(3-2-(2-Hydroxyheptyl)phenoxy)methyl pyridine hydrochloride.

EXAMPLE 23

Trans-3-hexanoyl stilbene

A mixture of α-bromo-m-tolunitrile (20 g) and triethylphosphite (29.1 g) was heated gently in a round-bottomed flask fitted with a distilling head. Ethyl bromide that formed was removed by distillation. When no more ethyl bromide was distilling, the residual liquid was distilled under reduced pressure to isolate the phosphonate as a clear, colorless liquid: 22 g, bp. 152°–154° C./0.02 mm.

The phosphonate (22 g) was dissolved in dry tetrahydrofuran, and added dropwise to a well-stirred suspension of sodium hydride (4.2 g; 50% oil suspension) in dry tetrahydrofuran. After the addition was complete, the mixture was stirred at room temperature for one hour, cooled in an ice bath, and then a solution of benzaldehyde (9.2 g) in dry tetrahydrofuran was added slowly. The mixture was allowed to warm up, and stirred at room temperature overnight. The excess of sodium hydride was destroyed by adding cold methanol, and then all volatiles were removed. The residue was taken up in ethyl acetate, and washed with HCl solution (5%), water and brine. The organic extract was dried and then all volatiles were removed. The crude product (18 g), trans-3-cyano stilbene, was isolated as a light orange solid, m.p. 69°–71° C.

To a solution of n-pentylmagnesium bromide (prepared from 1-bromopentane (7.3 g) and magnesium turnings (1.2 g) in tetrahydrofuran) was added a solution of the above cyano compound (9 g) in tetrahydrofuran, all at once. The resulting deep-red solution was refluxed for 8 hours. A solution of hydrochloric acid (6N) was added (24 ml) to the cold (0° C.) reaction mixture, and again refluxed for 8 hours. The mixture was cooled, and most tetrahydrofuran was removed at the rotary evaporator. The residue was dissolved in ethyl acetate, and the organic extract was washed with saturated sodium bicarbonate solution, brine, and then dried over magnesium sulfate. The solvent was removed to yield the crude material (15 g), which was purified by chromatography (silica gel; 3% ethyl acetate in hexanes). The desired trans-stilbene ketone was isolated as a white solid, m.p. 54°–56° C.

EXAMPLE 24

Trans-3-(1'hydroxyhexyl) Stilbene

The ketone, trans-3-hexanoyl stilbene of Example 23 (1 g) was dissolved in ethanol, and sodium borohydride (0.2 g) was added. The mixture was stirred overnight. Excess of the borohydride was destroyed by carefully adding a dilute HCl solution. The aqueous solution was extracted thoroughly with ether, and then the ether extract was washed with brine and dried. On removal of all volatiles, the pure alcohol was obtained as a clear, colorless liquid in quantitative yield.

In like manner as described above, using appropriate starting materials and reagents, the following compounds were prepared:
cis-3-(1-Hydroxyhexyl)stilbene;
1-(3-(2-Phenylethyl)phenyl-1-hexanol; and
3-(1-Hydroxyhexyl)diphenylacetylene.

EXAMPLE 25 cis-3-Hexanoyl Stilbene

To a solution of triphenylphosphine (29.5 g) in toluene (150 ml) was added a solution of α-bromo-m-tolunitrile (20 g) in toluene (50 ml), and the mixture was stirred at room temperature for one day. The white precipitate was filtered off and washed with toluene and ether to get the phosphonium bromide as a white solid.

The phosphonium salt (15 g) was dissolved in dry dimethylsulfoxide (100 ml), cooled to 0° C., and then a solution of n-butyl lithium in hexane (49.3 mmol) was added dropwise. The mixture became red and cloudy. It was allowed to warm up to room temperature in about one hour when the solution became completely clear. The homogeneous solution was cooled to 0° C., and a solution of benzaldehyde (3.8 g) in dimethylsulfoxide (50 ml) was added. The reaction mixture was stirred at room temperature overnight. Most dimethylsulfoxide was removed, and the residue was taken up in ether. The ether solution was washed with water, brine and dried. All solvent was removed and the crude material was chromatographed (silica gel; 5% ethyl acetate in hexanes). Cis-3-cyano stilbene was separated from the minor product which was the trans isomer.

Conversion of cis-3-cyano stilbene to the final product, cis-3-hexanoyl stilbene, was carried out in the same manner as described for the trans isomer, trans-3-hexanoyl stilbene in Example 23.

EXAMPLE 26

3-Hexanoyl diphenyl acetylene

Bromine (6.4 g) was added to a solution of trans-3-cyano stilbene (7.2 g) (Example 23) in chloroform (75 ml) and the mixture was refluxed overnight. The solution was washed with a 5% aqueous solution of sodium thiosulfate, water and then dried. On removal of all solvent, the desired stilbene dibromide was obtained as a light brown solid. This crude dibromide was dissolved in dry tetrahydrofuran, and potassium tert-butoxide (7.7 g) was added. The mixture was refluxed overnight. Most solvent was removed and the residue was taken up in ethyl acetate. The organic extract was washed with water, brine and dried. All solvent was removed to obtain the desired acetylenic compound, which was dissolved in ether; a minor impurity which was the corresponding amide, was removed by filtration. 3-Cyanodiphenyl acetylene (3.5 g) was isolated from the ethereal solution.

Conversion of 3-cyanodiphenylacetylene to the final product, 3-hexanoyl diphenyl acetylene, was performed as described under trans-3-hexanoyl stilbene in Example 23.

EXAMPLE 27

3-(2-Phenylethyl)hexanophenone

This compound was prepared by the catalytic reduction ($H_2$, 10% Pd-C, ethanol) of either trans-3-hexanoyl stilbene, cis-3-hexanoyl stilbene or, 3-hexanoyl diphenyl acetylene in nearly quantitative yield.

EXAMPLE 28

2-(3-(1-Hexenyl)phenoxy)methyl quinoline

Sodium ethoxide was prepared by dissolving sodium metal (0.9 g) in absolute ethanol (50 ml). 3-Hydroxybenzaldehyde (5 g) in alcohol (50 ml) was added to sodium ethoxide and the mixture was refluxed for one hour. The reaction mixture was cooled, and a solution of 2-chloromethyl quinoline (7.3 g) in alcohol (50 ml) was added. The mixture was refluxed for one day. All volatiles were removed, and the residue was taken up in ethyl acetate. The organic extract was washed with aqueous sodium hydroxide (5%) solution, water and brine. After drying, all solvent was removed. The residual oil was chromatographed on silic gel using 15% ethyl acetate in hexanes as eluent and the pure aldehyde was isolated.

n-Pentyl triphenylphosphonium bromide (3.1 g.), prepared by refluxing a toluene solution of 1-bromopentane and triphenylphosphine, and filtering the white phosphonium salt, was dissolved in tetrahydrofuran (100 ml). The solution was cooled to 0° C., and n-butyl lithium (7.6 mmol; 2.3M solution in hexane) was added. The mixture was stirred at room temperature for one hour, then cooled again to 0° C., and a solution of the above aldehyde (2 g) in tetrahydrofuran (35 ml) was added. The reaction mixture was stirred at room temperature overnight. Most tetrahydrofuran was removed, and the residue was taken up in ethyl acetate. The organic layer was washed with water, brine, and dried over magnesium sulfate. All solvents were removed, and the crude product was purified on silica gel using 15% ethyl acetate in hexanes as eluent. The desired compound was isolated as a light yellow liquid (0.8 g).

EXAMPLE 29

Methyl 3-(3-(1-hydroxyethyl)phenoxy)methyl benzoate

A mixture of 3-hydroxyacetophenone (7 g), methyl 3-bromomethyl benzoate (10 g), potassium carbonate (5 g) and potassium iodide (0.2 g) in acetone (75 ml) was refluxed overnight. The reaction mixture was poured into water, and extracted with ethyl acetate. The organic extract was washed with sodium hydroxide solution (1N), water, brine, and then dried. All volatiles were removed, and the residual pale yellow solid (11.5 g) was crystallized from ether. The pure product, methyl 3-(3-acetylphenoxy)methyl benzoate, was isolated as a white solid, m.p. 74.5°–75.5° C.

The above ketone (1.93 g) was dissolved in ethanol (50 ml), and sodium borohydride (0.07 g) was added. The reaction mixture was stirred at room temperature overnight. Excess sodium borohydride was destroyed with cold aqueous hydrochloric acid (1N). The reaction mixture was extracted thoroughly with ethyl acetate. The organic extract was washed with brine, dried over magnesium sulfate and then all solvent was removed. The crude product (1.9 g) was purified by chromatography to yield the desired compound as a colorless liquid.

EXAMPLE 30

3-(3-(1-Hydroxyethyl)phenoxy)methyl benzoic acid

This compound was made by hydrolyzing the corresponding methyl ester, methyl 3-(3-(1-hydroxyethyl)-phenoxy)methyl benzoate of Example 29 with sodium hydroxide solution. The desired compound was isolated as white crystals by crystallizing the crude acid from ether-ethanol, m.p. 115°–117° C.

The compounds of the present invention have potent activity in regulating the formation of lipoxgenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes B, C, and D, have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL FOR DETECTING INHIBITORS OF THE LIPOXYGENASE PATHWAY

A suspension of rat neutrophils in buffer is incubated for 3 minutes at 30° C. with [$^{14}$C]-arachidonic acid (AA) and Calcium Ionophore A23187. Citric Acid (2M) is used to quench the reaction. Following the addition of a trace amount of ($^3$H)-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isoctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantitated. The net pmoles of 5-HETE are obtained by substracting the pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced.

In Table I the last column shows the concentration required for 50% inhibition of the 5-lipoxygenase pathway (5-LOX/$I_{50}$ μM) for representative compounds according to the present invention.

TABLE I

ARYLEICOSANOIDS AS 5-LIPOXYGENASE INHIBITORS

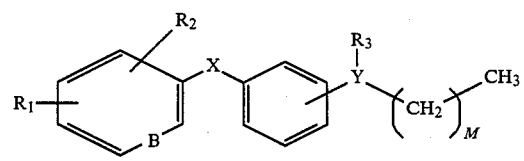

| No. | $R_1$ | $R_2$ | B | X | Y | $R_3$ | M | 5-LOX $I_{50}$ μM$^3$ |
|---|---|---|---|---|---|---|---|---|
| 1 | 3-CO$_2$H | H | C | CH$_2$O | 3-CHCH$_2$ | OH | 3 | 25 |
| 2 | 2-CO$_2$H | H | C | CH$_2$O | 3-CHCH$_2$ | OH | 3 | 30 |
| 3 | 2-CO$_2$H | H | C | CH$_2$O | 3-CHCH$_2$ | OH | 2 | 10 |
| 4 | 4-CO$_2$H | H | C | CH$_2$O | 3-CHCH$_2$ | OH | 3 | 21 |
| 5 | 3-CO$_2$CH$_3$ | H | C | CH$_2$O | 3-CHCH$_2$ | OH | 3 | 1.2 |
| 6 | 2-CO$_2$CH$_3$ | H | C | CH$_2$O | 3-CHCH$_2$ | OH | 3 | 0.6 |
| 7 | 2-CO$_2$CH$_3$ | H | C | CH$_2$O | 3-CHCH$_2$ | OH | 2 | 3.0 |
| 8 | 4-CO$_2$CH$_3$ | H | C | CH$_2$O | 3-CHCH$_2$ | OH | 3 | 3.2 |
| 9 | 3-CO$_2$CH$_3$ | H | C | CH$_2$O | 2-CHCH$_2$ | OH | 3 | 3.2 |
| 10 | 3-CH$_2$CO$_2$H | H | C | CH$_2$O | 3-CHCH$_2$ | OH | 3 | — |
| 11 | 3-CH$_2$CO$_2$CH$_3$ | H | C | CH$_2$O | 3-CHCH$_2$ | OH | 3 | 5.8 |

TABLE I-continued
ARYLEICOSANOIDS AS 5-LIPOXYGENASE INHIBITORS

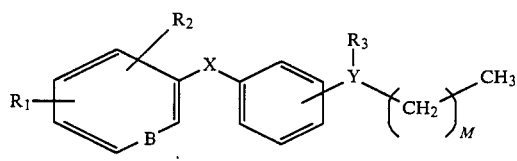

| No. | $R_1$ | $R_2$ | B | X | Y | $R_3$ | M | 5-LOX $I_{50} \mu M^3$ |
|---|---|---|---|---|---|---|---|---|
| 12 | 3-$CO_2CH_3$ | H | C | $CH_2O$ | 3-$CHCH_2$ | $OCOCH_3$ | 3 | 5.0 |
| 13 | 3-$CO_2CH_3$ | H | C | $CH_2O$ | 3-$CHCH_2$ | $OCH_3$ | 3 | 10 |
| 14 | 3-$CO_2CH_3$ | H | C | $CH_2O$ | 3-$CHCH_2$ | OTHP | 3 | 23 |
| 15 | 2-$CO_2CH_3$ | H | C | $CH_2O$ | 3-$CHCH_2$ | OTHP | 2 | 10 |
| 16 | 2-$CH_2OH$ | H | C | $CH_2O$ | 3-$CHCH_2$ | OH | 2 | 4 |
| 17 | 3-CHO | H | C | $CH_2O$ | 3-$CHCH_2$ | OH | 2 | 4.0 |
| 18 | 3-CN | H | C | $CH_2O$ | 3-$CHCH_2$ | OH | 3 | 17 |
| 19 | 3-$CH_2NH_2$ | H | C | $CH_2O$ | 3-$CHCH_2$ | OH | 3 | — |
| 20 | 3-$CONH_2$ | H | C | $CH_2O$ | 3-$CHCH_2$ | OH | 3 | 2.0 |
| 21 | 4-$OCH_2CO_2CH_3$ | H | C | $CH_2O$ | 3-$CHCH_2$ | OH | 3 | 4.8 |
| 22 | H | H | C | $CH_2O$ | 3-$CHCH_2$ | OH | 3 | 2.7 |
| 23 | H | H | C | $OCH_2$ | 3-$CHCH_2$ | OH | 3 | 6.7 |
| 24 | 3-$CO_2CH_3$ | H | C | $CH_2O$ | 3-CH=CH | $CH_3$ | 3 | 5.0 |
| 25 | 3-$CO_2CH_3$ | H | C | $CH_2O$ | 4-CH=CH | H | 3 | 100 |
| 26 | H | H | C | $CH_2O$ | 3-C—$CH_2$ | O | 3 | 2.0 |
| 27 | H | H | 4-N | $CH_2O$ | 3-$CHCH_2$ | OH | 3 | 2.7 |
| 28 | H | H | 2-N | $CH_2O$ | 3-$CHCH_2$ | OH | 3 | 0.5 |
| 29 | H | H | 3-N | $CH_2O$ | 3-$CHCH_2$ | OH | 3 | 2.7 |
| 30 | 3-CN | H | 2-N | $CH_2O$ | 3-$CHCH_2$ | OH | 3 | 30 |
| 31 | 3-$CO_2CH_3$ | H | 2-N | $CH_2O$ | 3-$CHCH_2$ | OH | 3 | 3.0 |
| 32 | 3-$CO_2H$ | H | 2-N | $CH_2O$ | 3-$CHCH_2$ | OH | 3 | 6.0 |
| 33 | (fused ring 3,4) | | 2-N | $CH_2O$ | 3-$CHCH_2$ | OH | 3 | 0.3 |
| 34 | H | H | C | $CH_2O$ | 3-$CC(CH_3)_2$ | O | 3 | 7.5 |
| 35 | H | H | C | $CH_2O$ | 3-$CHC(CH_3)_2$ | OH | 3 | 2.5 |
| 36 | H | H | C | $CH_2O$ | 3-$CHC(CH_3)$ | OH | 3 | 3.0 |
| 37 | 3-$CO_2CH_3$ | H | C | $CH_2O$ | 3-$CHC(CH_3)_2$ | OH | 3 | 2.0 |
| 38 | (fused ring 3,4) | — | 2-N | $CH_2O$ | 3-C—$CH_2$ | O | 3 | 0.15 |
| 39 | H | H | C | $CH_2O$ | 3-$C(CH_3)CH_2$ | OH | 3 | 1.0 |
| 40 | H | H | C | $CH_2O$ | 3-$C(CH_3)C(CH_3)_2$ | OH | 3 | 2.4 |
| 41 | (fused ring 3,4) | — | 2-N | $CH_2O$ | 3-$C(CH_3)CH_2$ | OH | 3 | 0.1 |
| 42 | H | H | 2-N | $CH_2O$ | 3-$C(CH_3)CH_2$ | OH | 3 | 0.3 |
| 43 | H | H | C | $CH_2O$ | 3-$CHCH_2$ | $NHCH_3$ | 3 | 22 |
| 44 | H | H | C | trans CH=CH | 3-$CHCH_2$ | OH | 3 | 4.5 |
| 45 | (fused ring 3,4) | — | 2-N | $CH_2O$ | 3-C≡CH | H | 3 | 2.4 |
| 46 | 3-$CONH_2$ | H | C | $CH_2O$ | 3-$CCH_2$ | O | 3 | 0.7 |
| 47 | 3-CN | H | C | $CH_2O$ | 3-$CCH_2$ | O | 3 | 8.0 |
| 48 | H | H | C | O | 3-$CHCH_2$ | OH | 3 | 1.2 |
| 49 | 3-$CF_3$ | H | C | $CH_2O$ | 3-$CHCH_2$ | OH | 3 | 3.0 |

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. The following protocol describes an in vitro assay used to test compounds which specifically antagonize the actions of leukotrienes.

PROTOCOL FOR SRS-A (SLOW-REACTING SUBSTANCE OF ANAPHYLAXIS) ANTAGONISTS

Peripheral strips of guinea pig lungs are prepared and hung in tissue baths (Metro #ME-5505, 10 ml) according to the published procedure (Proc. Nat'l Acad. Sci, U.S.A. Volume 77, pp. 4354-4358, 1980). The strips are thoroughly rinsed in Assay Buffer and then connected with surgical silk thread to the support rods from the tissue baths. The rods are adjusted in the baths and the strips connected to the pressure transducers (Grass FT 103 or Gould UC-3). The tissue baths are aerated with 95% oxygen—5% carbon dioxide and maintained at 37° C. The Assay Buffer has been made as follows: For each liter of buffer the following are added to approximately 800 ml of water distilled in glass—6.87 g. NaCl, 0.4 g. KCl, 2.1 g. $NaHCO_3$, 0.14 g. $NaH_2PO_4 \cdot H_2O$, 0.21 g. $MgSO_4 \cdot 7H_2O$, and 2.0 g. D-glucose. Then a solution of 0.368 g. $CaCl_2 \cdot 2H_2O$ in 100 ml glass-distilled water is slowly added to the buffer. Sufficient water is added to adjust the volume to one liter, and the solution is aerated with 95% oxygen—5% carbon dioxide. Usually 10 liters of buffer are used for an experiment with 4 tissues.

After the tissues have been repeatedly washed and allowed to equilibrate in the tissue bath, they are challenged with 1 µM histamine. After maximum contractions have been obtained, the tissues are washed, and allowed to relax back to baseline tension. This histamine challenge procedure is repeated at least 1 to 2 more time to obtain a repeatable control response. The average response to 1 µM histamine for each tissue is used to normalize all other challenges.

Responses of each tissue to a pre-determined concentration of leukotriene are then obtained. Usually test compounds are examined initially at 30 µM on resting tension of the tissues without any added agonist or antagonist to determine if the compound has any possible intrinsic activity. The tissues are washed, and the test compound is added again. Leukotriene is added after the desired pre-incubation time. The intrinsic activity of the compounds, and their effect on leukotriene-induced contractions are then recorded.

The concentration required for 50% inhibition of 0.2 nM leukotriene $C_4$—induced contraction of guinea pig peripheral strips for representative compounds of the present invention is shown in Table II.

TABLE II

| ARYLEIOCOSANOIDS AS SRS-A Antagonists | |
|---|---|
| No.* | SRS-A Antagonist $I_{50}$ µM |
| 2 | 20 |
| 3 | 20 |
| 10 | 40 |
| 29 | 8 |
| 33 | 3 |
| 41 | 7 |
| 48 | 30 |

*Numbers correspond to numbers and compounds identified by their chemical structures in Table I.

Representative compounds of the present invention were also tested in the following in vivo model.

PROTOCOL FOR IN VIVO TESTING OF MODULATORS OF SRS-S (SLOW REACTING SUBSTANCES OF ANAPHYLAXIS)

This test, known as the Bronchial Anaphylaxis in Guinea Pigs with Enhanced Leukotrines (BAGEL), is based on the procedure published in Agents and Actions, Vol. 11, pp. 396-401, 1981, and is performed with guinea pigs actively immunized (14 days) with ovalbumin (2.7 mg/kg, i.p.) and B.pertussis ($5 \times 10^9$ organisms) as an adjuvant. Prior to challenge with antigen (ovalbumin), the animals are anesthetized and prepared for monitoring pulmonary dynamics by whole body plethysmography. They are treated with an $H_1$ antihistamine (methapyrilene, 2 mg/kg, i.v.) and cyclooxygenase inhibitor (indomethacin; 20 mg/kg, i.p.) in order to enhance the SRS-A component of anaphylactic bronchoconstriction. Bronchoconstriction is quantified as the maximum increase in airway resistance following antigen challenge. The drug is administered either i.p. 10 minutes before challenge, or i.d. 15 minutes before challenge.

In Table III are shown results of testing a few compounds of the present invention according to this protocol.

TABLE III

| ARYLEICOSANOIDS AS SRS-A MODULATORS | |
|---|---|
| No.* | BAGEL |
| 20 | H at 200 mg/Kg, i.d. |
| 24 | M at 100 mg/Kg, i.v. |
| 33 | H at 6 mg/Kg, i.d. |
| 41 | M at 200 mg/Kg, i.d. |
| 48 | H at 200 mg/Kg, i.p. |

*Numbers correspond to numbers and compounds identified by their chemical structures in Table I.

Rating System (mean of $\geq 2$ trials):
H: <150% increase in airway resistance
M: 150-300% increase in airway resistance The therapeutic compounds of this invention may be administered to a mammal alone or in combination with pharmaceutically acceptable carriers, the proportion of which is determined by the solubility and chemical nature of the compound, chosen route of administration and standard pharmaceutical practice.

The physician will determine the dosage of the present therapeutic agents which will be most suitable and it will vary with the form of administration and the particular compound chosen, and also, it will vary with the particular patient under treatment. He will generally wish to initiate treatment with small dosages substantially less than the optimum dose of the compound and increase the dosages by small increments until the optimum effect under the circumstances is reached. The therapeutic dosage will generally be from 0.1 to 100 µM per day and higher although it may be administered in several different dosage units.

What is claimed:
1. A compound of the formula:

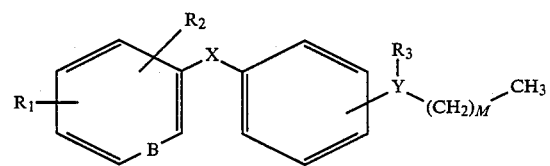

and pharmaceutically acceptable salts thereof, wherein $R_1$ and $R_2$ are each independently H, an alkyl group having from 1 to about 6 carbon atoms, and one of the terms $R_1$ and $R_2$ may comprise $CF_3$; COOH; COO-lower alkyl or $R_1$ and $R_2$ combine with the six-membered ring to which they are attached to form naphthyl; quinoline or isoquinoline;

B is C or N;

X is CH₂O

Y is CHCH₂ or C(R₅)CH₂ wherein R₅ is H or lower alkyl;

R₃ is OH;

M is an integer from about 2 to about 3.

2. A compound of claim 1 of the formula

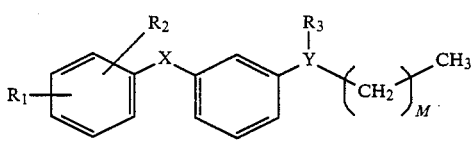

and pharmaceutically acceptable salts thereof, wherein X, Y, R₃ and M are as defined previously in claim 1.

3. A compound of claim 1 of the formula

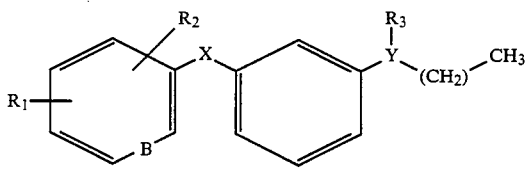

and pharmaceutically acceptable salts thereof, wherein:

B is N; and

X, Y, R₃ and M are as previously defined in claim 1.

4. A compound of claim 1 of the formula

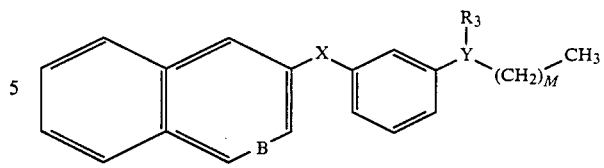

and the pharmaceutically acceptable salts thereof, wherein:

B is N; and

X, R₃ and M are as previously defined in claim 1.

5. The compound methyl 3-[[3-(1-hydroxyhexyl)-phenoxy]methyl]benzoate.

6. The compound, methyl 2-[[3-(1-hydroxyhexyl)-phenoxy]methyl]benzoate.

7. The compound, 1-(3-benzyloxyphenyl)-1-methyl-1-pentanol.

8. The compound, 2-[[3-(1-hydroxyhexyl)phenoxy]-methyl]pyridine and the pharmaceutically acceptable salts thereof.

9. The compound, 2-[[3-(1-hydroxyhexyl)phenoxy]-methyl]pyridine hydrochloride.

10. The compound, 2-[[3-(1-hydroxhexyl)phenoxy]-methyl]quinoline and the pharmaceutically acceptable salts thereof.

11. The compound, 2-[[3-(1-hydroxyhexyl)phenoxy]-methyl]quinoline hydrochloride.

12. The compound, 2-(3-(2-hydroxyheptyl)phenoxy)-methyl quinoline and the pharmaceutically acceptable salts thereof.

13. The compound, 2-(3-(2-hydroxyheptyl)phenoxy)-methyl quinoline hydrochloride.

14. The compound, 2-[[3-(1-hydroxy-1-methylhexyl)-phenoxy]methyl]quinoline and the pharmaceutically acceptable salts thereof.

15. The compound, 2-[[3-(1-hydroxy-1-methylhexyl)-phenoxy]methyl]pyridine and the pharmaceutically acceptable salts thereof.

16. A method of treating inflammatory and allergic conditions in a mammal by administering to said mammal an effective amount of a compound of claim 1.

* * * * *